(12) United States Patent
Irani (10) Patent No.: US 8,547,556 B2
(45) Date of Patent: Oct. 1, 2013

(54) METHODS OF ANALYZING A RESERVOIR FLUID SAMPLE USING A MULTIVARIATE OPTICAL ELEMENT CALCULATION DEVICE

(75) Inventor: Cyrus A. Irani, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 13/542,078

(22) Filed: Jul. 5, 2012

(65) Prior Publication Data

US 2013/0155408 A1 Jun. 20, 2013

Related U.S. Application Data

(63) Continuation of application No. PCT/US2011/064763, filed on Dec. 14, 2011.

(51) Int. Cl.
*G01N 21/55* (2006.01)
*G01N 21/00* (2006.01)

(52) U.S. Cl.
USPC .......................................... 356/445; 356/439

(58) Field of Classification Search
USPC ......... 356/244–246, 337–343, 436, 440–442, 356/445–448
See application file for complete search history.

(56) References Cited

U.S. PATENT DOCUMENTS

| 7,210,343 | B2 * | 5/2007 | Shammai et al. .......... 73/152.28 |
| 7,697,141 | B2 | 4/2010 | Jones et al. |
| 2009/0002697 | A1 | 1/2009 | Freese et al. |
| 2009/0107667 | A1 | 4/2009 | Mullins et al. |
| 2009/0219539 | A1 * | 9/2009 | Myrick et al. ............. 356/445 |
| 2010/0245096 | A1 | 9/2010 | Jones et al. |

FOREIGN PATENT DOCUMENTS

WO 2011146068 A1 11/2011

* cited by examiner

*Primary Examiner* — Tara S Pajoohi Gomez
(74) *Attorney, Agent, or Firm* — Scott Wendorf; Sheri Higgins Law; Sheri Higgins (57) ABSTRACT

A method of analyzing a fluid sample from a reservoir comprises: collecting the sample in a sampling container, wherein the sample container includes a sample receptacle, and wherein the step of collecting comprises allowing or causing the sample to flow into the sample receptacle; and determining at least one property of the sample, wherein the step of determining comprises using a multivariate optical element (MOE) calculation device, and wherein the step of determining is performed during the step of collecting and wherein the MOE calculation device is located at one end of the sample receptacle, or the step of determining is performed after the step of collecting. The sample is analyzed as the sample flows into the sample container or as the sample is being transferred from the sample container into a container.

17 Claims, 5 Drawing Sheets

METHODS OF ANALYZING A RESERVOIR FLUID SAMPLE USING A MULTIVARIATE OPTICAL ELEMENT CALCULATION DEVICE

CROSS-REFERENCE TO RELATED APPLICATION

This application is a continuation of and claims priority to International Application No. PCT/US11/64763, filed Dec. 14, 2011.

TECHNICAL FIELD

A method of analyzing a sample using a multivariate optical element (MOE) calculation device is provided. According to an embodiment, the sample is a reservoir fluid. The sample can be analyzed during or after collection of the sample. The sample can be analyzed for at least one property of the fluid. According to an embodiment, the sample is analyzed for two or more properties of the fluid.

SUMMARY

According to an embodiment, a method of analyzing a fluid sample from a reservoir comprises: collecting the sample in a sampling container, determining at least one property of the sample, wherein the step of determining comprises using a multivariate optical element (MOE) calculation device, and wherein the step of determining is performed during or after the step of collecting.

BRIEF DESCRIPTION OF THE FIGURES

The features and advantages of certain embodiments will be more readily appreciated when considered in conjunction with the accompanying figures. The figures are not to be construed as limiting any of the preferred embodiments.

DETAILED DESCRIPTION

As used herein, the words "comprise," "have," "include," and all grammatical variations thereof are each intended to have an open, non-limiting meaning that does not exclude additional elements or steps.

It should be understood that, as used herein, "first," "second," "third," etc., are arbitrarily assigned and are merely intended to differentiate between two or more MOE devices, heating elements, etc., as the case may be, and does not indicate any sequence. Furthermore, it is to be understood that the mere use of the term "first" does not require that there be any "second," and the mere use of the term "second" does not require that there be any "third," etc.

As used herein, a "fluid" is a substance having a continuous phase that tends to flow and to conform to the outline of its container when the substance is tested at a temperature of 71° F. (22° C.) and a pressure of one atmosphere "atm" (0.1 megapascals "MPa"). A fluid can be a liquid or gas. A fluid can have only one phase or more than one phase. In the oil and gas industry, a fluid having only one phase is commonly referred to as a single-phase fluid and a fluid having more than one phase is commonly referred to as a multi-phase fluid. A colloid is an example of a multi-phase fluid. A colloid can be: a slurry, which includes a continuous liquid phase and undissolved solid particles as the dispersed phase; an emulsion, which includes a continuous liquid phase and at least one dispersed phase of immiscible liquid droplets; a foam, which includes a continuous liquid phase and a gas as the dispersed phase; or a mist, which includes a continuous gas phase and liquid droplets as the dispersed phase.

Oil and gas hydrocarbons are naturally occurring in some subterranean formations. A subterranean formation containing oil or gas is sometimes referred to as a reservoir. A reservoir may be located under land or off shore. In order to produce oil or gas, a wellbore is drilled into a reservoir or adjacent to a reservoir.

A well can include, without limitation, an oil, gas, or water production well, or an injection well. As used herein, a "well" includes at least one wellbore. A wellbore can include vertical, inclined, and horizontal portions, and it can be straight, curved, or branched. As used herein, the term "wellbore" includes any cased, and any uncased, open-hole portion of the wellbore. A near-wellbore region is the subterranean material and rock of the subterranean formation surrounding the wellbore. As used herein, a "well" also includes the near-wellbore region. As used herein, the phrase "into a well" includes into any portion of the wellbore or into the near wellbore region via the wellbore.

In the oil and gas industry it is often desirable to analyze a portion of a reservoir fluid because a reservoir fluid can contain one or more substances that might be detrimental to wellbore operations. For example, a wellbore fluid can contain a corrosive substance that might be harmful to wellbore equipment, such as pumping equipment or pipes. Examples of corrosive substances include, but are not limited to, high amounts of an acid gas, such as carbon dioxide gas (acid gas wells) and wells containing high amounts of a sour gas, such as hydrogen sulfide gas (sour gas wells).

Another potentially detrimental substance is an asphaltene. If asphaltenes are present in the reservoir fluid, then generally they are in solution due to being stabilized by resins. However, if the relative resin content decreases, then the asphaltenes may precipitate out of the fluid and deposit on pipe walls, restricting or interrupting fluid flow. It is relatively costly to remove such asphalt deposits, which may require grinding or scraping operations for removal. Other potentially detrimental substances are aromatics and naphthanates. When combined with water, aromatics and naphthanates can cause foaming of the solution, somewhat like when water is combined with soap. The foam can also restrict or interrupt fluid flow.

Another potentially detrimental substance is a gas hydrate. Generally, a substance containing between one and six carbon atoms ($C_1$ to $C_6$) is a gas at wellbore temperatures and pressures. However, during wellbore operations, depending on the temperature at the wellhead, some or all of the gas may form gas hydrates. Gas hydrates occur naturally onshore in permafrost regions, and at certain depths in the sea where water and gas combine at low temperatures and high pressures to form the hydrate. Methane ($C_1$), or natural gas, is typically the dominant gas in the hydrate structure. As gas emerges from the wellhead, water molecules from the surrounding environment form a cage-like structure around high concentrations of the gas molecules and freeze into a solid gas/water structure. If a sufficient amount of gas hydrates form, the hydrates can block or clog valves and pipes leading to the surface from the cap. As such it may be desirable to test a reservoir fluid for its gas-to-oil (GOR) ratio. This ratio, along with the temperature at the wellhead, can be useful in predicting the likelihood of gas hydrate formation.

There are several devices that can be used to analyze a fluid. Some devices are designed to be used in a laboratory setting and other devices can be used in a well or at or near the well site. An example of an analyzer that can be used to analyze a fluid is a multivariate optical element (MOE) calculation device. The MOE calculation device is described fully in U.S. Pat. No. 7,697,141 B2, issued on Apr. 13, 2010 to Jones, et al., which is hereby incorporated by reference in its entirety for all purposes. If there is any conflict in the usages of a word or term in this specification and one or more patents or other documents that may be incorporated herein by reference, then the definitions that are consistent with this specification control and should be adopted.

The MOE calculation device can be used to analyze a fluid sample for a variety of substances and/or fluid properties. For example, the MOE calculation device, without in any way limiting its scope, can be used for determining asphaltenes, saturates, resins, aromatics, solid particulate content, hydrocarbon composition and content, gas composition $C_1$-$C_6$ and content, $CO_2$, $H_2S$ and correlated PVT properties including GOR, bubble point, density, a petroleum formation factor, viscosity, a gas component of a gas phase of the petroleum, total stream percentage of water, gas, oil, solid particles, solid types, oil finger printing, reservoir continuity, oil type, and water elements including ion composition and content, anions, cations, salinity, organics, pH, mixing ratios, tracer components, contamination, or other hydrocarbon, gas, solids or water property that can be related to spectral characteristics using regression methods.

It is often desirable to take a sample of a reservoir fluid. There are a variety of instruments that can be used to collect a sample of formation fluids. One such instrument is the ARMADA® sampling system, marketed by Halliburton Energy Services, Inc. In order to collect a sample, the sampling system is placed into a wellbore at a desired location. The sampling system functions to collect multiple samples of the reservoir fluid at that location. The ARMADA® sampling system is currently able to collect up to nine unique samples of the reservoir fluid per trip. The sampling system is then returned to the surface where the samples can be retrieved from the system.

A collected sample is generally sent to a laboratory off-site for analysis. It can be quite costly to analyze each collected sample. Furthermore, the sampling containers may not be compliant with a country's transportation regulations. In these instances, the sample is often times transferred into a shipping container that is regulation compliant. It can be expensive and time consuming to transfer multiple samples to compliant containers for laboratory analysis.

It would be advantageous to analyze a reservoir fluid sample either during collection or after collection and prior to transportation of the sample to an off-site laboratory. By being able to analyze collected samples prior to shipment to the off-site laboratory, more informed decisions can be made at the well site, such as which, if any, samples should be sent off-site for further analysis. Being able to reduce the total number of samples sent off-site can save money and time. Thus, there is a need for analyzing a reservoir fluid sample for at least one property during collection or after collection, but prior to the sample being transported off-site.

According to an embodiment, a method of analyzing a fluid sample from a reservoir comprises: collecting the sample in a sampling container, determining at least one property of the sample, wherein the step of determining comprises using a multivariate optical element (MOE) calculation device, and wherein the step of determining is performed during or after the step of collecting.

Any discussion of the embodiments regarding the analysis of the sample is intended to apply to all of the method embodiments. Any discussion of a particular component of an embodiment (e.g., a heating element) is meant to include the singular form of the component and also the plural form of the component, without the need to continually refer to the component in both the singular and plural form throughout. For example, if a discussion involves "the heating element 90," it is to be understood that the discussion pertains to one heating element (singular) and two or more heating elements (plural).

Figure 1:
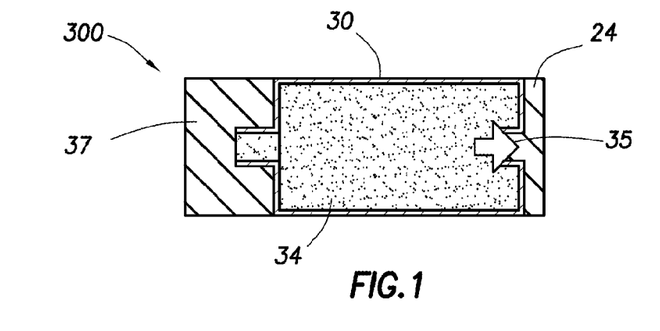
FIG. 1 is a diagram of a sample container including a sample receptacle.

Turning to the Figures. FIG. 1 depicts a sample container 300 according to an embodiment. The methods include the step of collecting a sample in the sample container 300. According to an embodiment, the sample container 300 is part of the ARMADA® sampling system, marketed by Halliburton Energy Services, Inc. The sample container 300 can include a sample receptacle 30. The sample receptacle 30 can have two ends; a first end and a second end. The sample receptacle 30 can include a first opening. The sample receptacle 30 can also include a second opening. The openings can be located at the first and second ends. The sample receptacle 30 can contain the sample 34. The sample 34 can be collected in the sample container 300 by introducing the sample 34 into the sample receptacle 30 via the first and/or second openings. The sample 34 can be a substance, such as a solid, liquid, gas, or combinations thereof. For example, the sample can be a slurry, emulsion, foam, or mist. According to an embodiment, the sample is a reservoir fluid.

The sample container 300 can further comprise a valve 35. The valve 35 can be a one-way valve. As used herein, the term "one-way valve" means a device that allows a fluid to enter a space within an enclosed area in one direction, but does not independently allow the fluid to exit the space in a reverse direction. Of course, a one-way valve may have a release mechanism whereby a person can activate the mechanism thereby causing at least some of the fluid within the sample retaining space to flow out of the enclosed area. However, the one-way valve should be designed such that any fluid that enters the space will not freely flow back out of that space without external intervention. As can be seen in FIG. 1, the valve 35 can be positioned in a first opening of the sample receptacle 30. More than one valve 35 can be located in the sample receptacle 30. A sample can be introduced into the sample receptacle 30 via the valve 35 positioned in the first opening of the sample receptacle 30. In this manner, the sample can be contained inside the sample receptacle 30 until such time when it is desirable to remove the sample from the sample receptacle 30. The sample container 300 can further include a pressurization compartment (not shown). The pressurization compartment can be used to help maintain the sample 34 in a single phase.

The sample container 300 can further comprise at least one seal 37. The seal 37 can be positioned adjacent to the sample receptacle 30. The seal 37 can be positioned at either end of the sample receptacle 30. The sample container 300 can also include two or more seals. One seal 37 can be positioned at the first end of the sample receptacle 30 and the other seal (not shown) can be positioned at the second end of the sample receptacle 30. According to an embodiment, the seal is designed such that once in place, a sample located within the sample receptacle 30 is not capable of independently exiting the sample receptacle 30. By including two or more seals, any sample located within the sample receptacle 30 can be contained.

The seal 37 can be permanently or removably attached to the sample container 300. By way of example, the seal 37 can be removably attached to the sample receptacle 30. In this manner, once a sample has been collected and is located inside the sample receptacle 30, the sample can be contained within the sample receptacle 30 by attaching the seal 37 to an end of the sample receptacle 30. Moreover, in the event it is desirable to remove the sample 34 from the sample receptacle 30, then the seal 37 can be removed. The seal 37 can include an opening.

The methods include the step of collecting the sample 34 in the sample container 300. The step of collecting can include placing the sample container 300 into a well. The step of collecting can further comprise allowing or causing the sample 34 to flow into the sample receptacle 30. The methods can further include the step of removing the sample container 300 from the well, wherein the step of removing can be performed after the step of collecting. By way of example, once the sample 34 is collected, the sample container 300 can be returned to the surface. The methods can further include the step of retrieving the sample receptacle 30 from the sample container 300, wherein the step of retrieving is performed after the step of collecting and/or after the step of removing. The methods can further include the step of attaching one or more seals 37 to the ends of the sample receptacle 30, wherein the step of attaching is performed after the step of retrieving. In this manner, the sample 34 can be contained within the sample receptacle 30. The sample 34 can then be stored, analyzed, transferred, or transported to an off-site location.

The methods include the step of determining at least one property of the sample 34. The at least one property can be selected from the group consisting of: asphaltenes; saturates; resins; aromatics; solid particulate content; hydrocarbon composition and content; gas composition $C_1$-$C_{13}$ and content; carbon dioxide; hydrogen sulfide gas; and correlated pressure, volume, temperature properties including gas-to-oil ratio, bubble point, density, a petroleum formation factor, viscosity, a gas component of a gas phase of a petroleum, total stream percentage of water, gas, oil, solid particles, solid types, oil finger printing, reservoir continuity, oil type; and water elements including ion composition and content, anions, cations, salinity, organics, pH, mixing ratios, tracer components, contamination; or other hydrocarbon, gas, solids, or water properties that can be related to spectral characteristics using regression methods.

Figure 2:
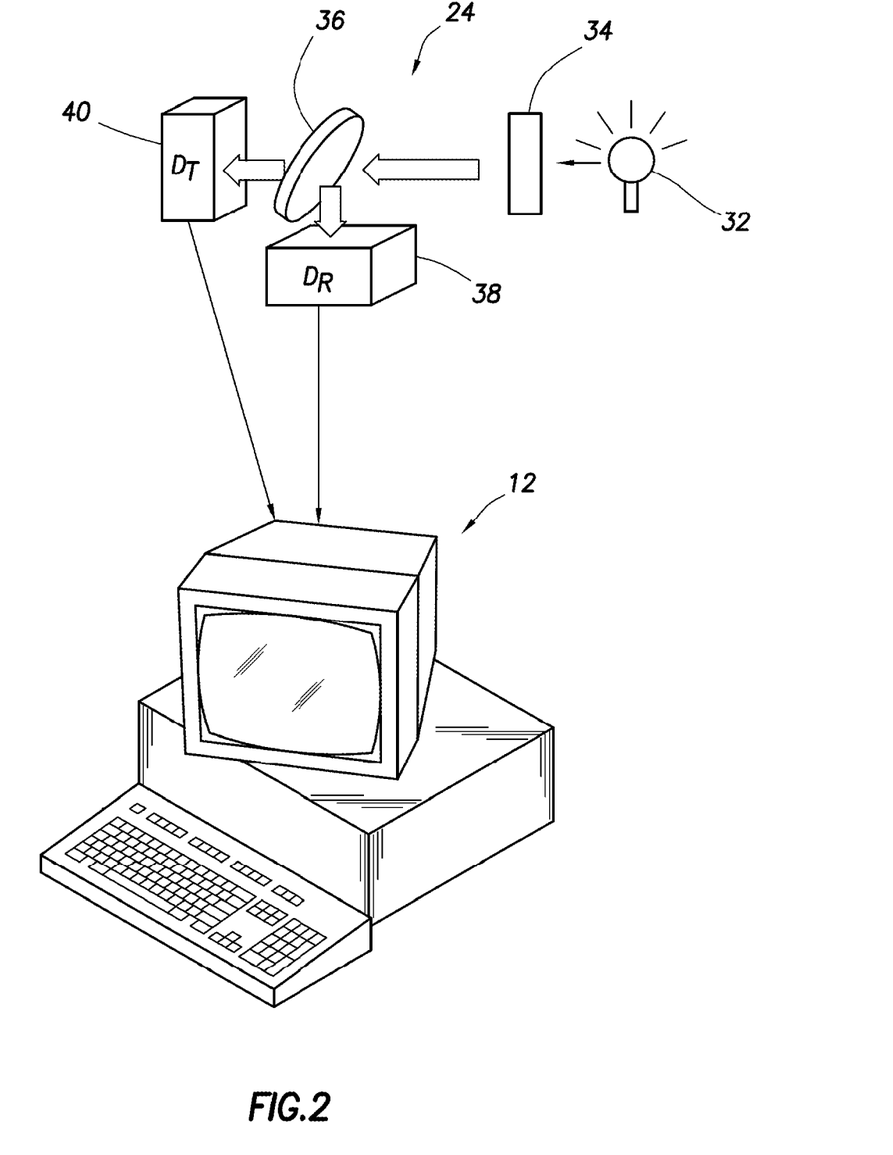
FIG. 2 is a diagram of a MOE calculation device for analyzing one or more properties of a sample.

The step of determining comprises using a multivariate optical element (MOE) calculation device. FIG. 2 depicts a multivariate optical element calculation device 24 according to an embodiment. Representative device 24 comprises: a light source 32; the sample 34; a multivariate optical element (MOE) 36, which is an optical regression calculation device; a detector 38 for detecting light reflected from MOE 36; and a detector 40 for detecting the light transmitted by MOE 36. The MOE is a unique optical calculation device that comprises multiple layers.

Figure 3:
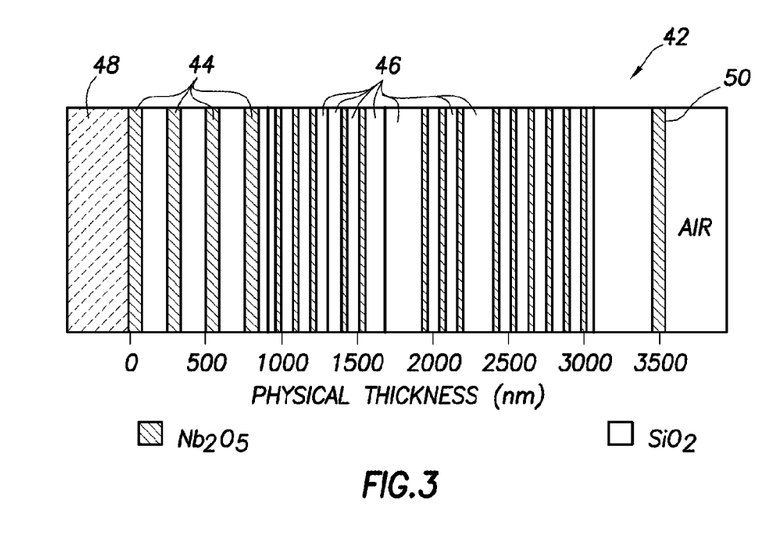
FIG. 3 is a side elevation sectional view of an illustrative representative MOE filter construction.

In FIG. 3, for example, representative optical regression calculating device MOE 42 comprises a plurality of alternating layers 44 and 46 respectively of $Nb_2O_5$ and $SiO_2$ (quartz). The layers are deposited on a glass substrate 48 which may be of the type referred to in this art as BK-7. The other end layer 50 of the optical calculating layers is exposed to the environment of the installation. The number of layers and the thickness of the layers are determined from, and constructed from, the spectral attributes determined from a spectroscopic analysis of a property of the sample 34 using a conventional spectroscopic instrument. The combination of layers corresponds to the signature of the property of interest according to the spectral pattern of that property.

The spectrum of interest of a given property typically comprises any number of different wavelengths. It should be understood that the MOE of FIG. 3 does not in fact represent any property of a sample 34, such as a reservoir fluid, but is provided for purposes of illustration only. The number of layers and their relative thicknesses of FIG. 3 thus bear no correlation to any sample 34 property to which the present invention is directed and are also not to scale. The thickness of the layers may be in the order of microns each as shown.

The multiple layers can have different refractive indices. By properly selecting the materials of the layers and their spacing, the optical calculation device can be made to selectively pass predetermined fractions of light at different wavelengths. Each wavelength is given a predetermined weighting or loading factor. The thicknesses and spacing of the layers may be determined using a variety of approximation methods from the spectrograph of the property of interest. The approximation methods may include inverse Fourier transform (IFT) of the optical transmission spectrum and structuring the optical calculation device as the physical representation of the IFT. The approximations convert the IFT into a structure based on known materials with constant refractive indices.

The weightings that the MOE 42 layers apply at each wavelength are set to the regression weightings described with respect to a known equation, or data, or spectral signature which can be found for the given property of interest. The optical calculation device MOE 42 performs the dot product of the input light beam into the optical calculation device and a desired loaded regression vector represented by each layer for each wavelength. The MOE 42 output light intensity is directly related to, and is proportional to, the desired sample 34 property. The output intensity represents the summation of all of the dot products of the passed wavelengths and corresponding vectors.

By way of example, if the property of interest is resin in a reservoir fluid sample, and the regression vectors are that of the resin, then the intensity of the light output of the MOE is proportional to the amount of resin in the sample through which the light beam input to the optical calculation device has either passed or has been reflected from or otherwise interacted with. The ensemble of layers corresponds to the signature of resin. These wavelengths are weighted proportionately by the construct of the corresponding optical calculation device layers. The resulting layers together produce an optical calculation device MOE 42 output light intensity from the input beam. The output light intensity represents a summation of all of the wavelengths, dot products, and the loaded vectors of that property, e.g., resin. The output optical calculation device's intensity value is proportional to the amount of resin in the sample 34 being analyzed. In this way an MOE optical calculation device is produced for each property to be determined in the sample 34.

Such MOE optical calculation devices represent pattern recognition devices which produce characteristic output patterns representing a signature of the spectral elements that define the property of interest. The intensity of the light output is a measure of the proportional amount of the property in the test media being evaluated. For example, an MOE transmission output waveform might appear as in FIGS. 4 and 5, which do not represent any specific sample property, but are shown for purposes of illustration only. The waveform of FIG. 4 forms a pattern comprising different wavelengths of a spectrum that is unique to a given property. This waveform may be the light that impinges upon detector 40 of FIG. 2, for example. Each of these detectors, such as detectors 38 and 40 associated with MOE 36, transmits its output, an electrical signal, which represents the magnitude of the intensity of the signal of FIG. 4 that is incident on the detector. Thus, this signal is a summation of all of the intensities of the different wavelengths incident on the detector. The various weighting factors assigned to each layer produce a composite signature waveform for that property.

Figure 4:
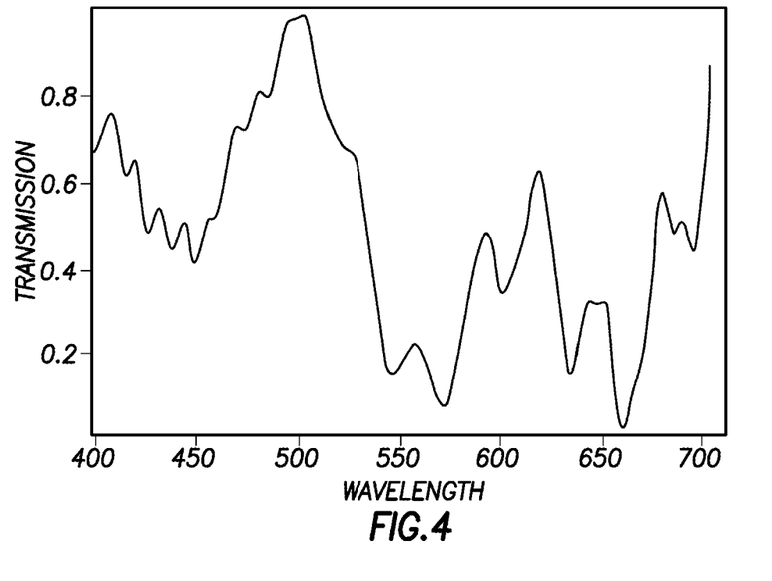
FIGS. 4 and 5 are graphs illustrating respective transmission and reflectance light intensity signature patterns of an illustrative substance property passed by a multilayered MOE filter.
Figure 5:
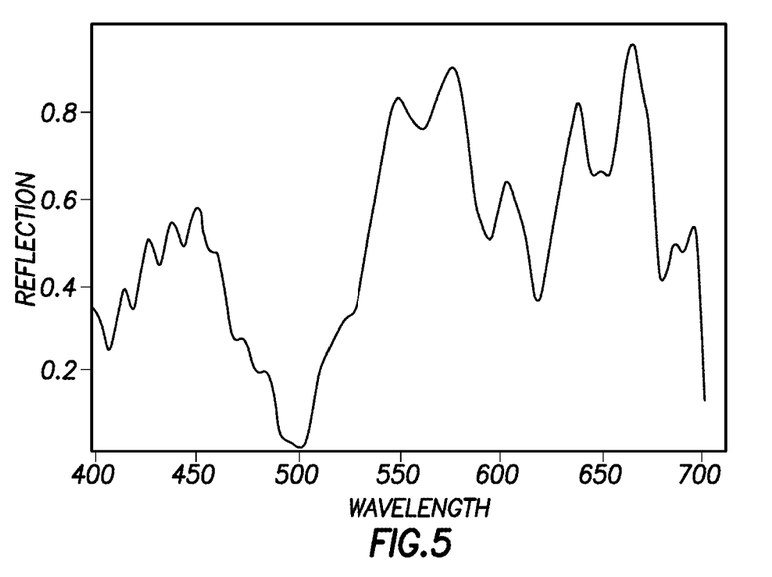

The reflected light from the MOE 36 of FIG. 2, produces a negative of the transmitted signal of FIG. 4 for no sample or optical absorbance. This reflected signal is represented by the waveform of FIG. 5 and is not a regression calculation. The reflected signal is subtracted from the transmitted signal of FIG. 4 by the computer 12 of FIG. 2. The difference represents the magnitude of the net light intensity output from the MOE and the property in the sample being examined. This subtraction provides correlation that is independent of fluctuations of the intensity of the original light due to power fluctuations, or use of different light bulbs, but of the same type as used in the original apparatus. That is, if the transmitted light intensity varies due to fluctuations, the system could interpret this as a change in property. By subtracting the negative reflections, the result is an absolute value independent of such fluctuations, and thus, provides needed correlation to the desired property being determined. Either the raw detector outputs may be sent to a computer, or the signals may be subtracted with an analog circuit and magnified with an operational amplifier converted to voltage and sent to the computer as a proportional signal, for example.

Figure 6:
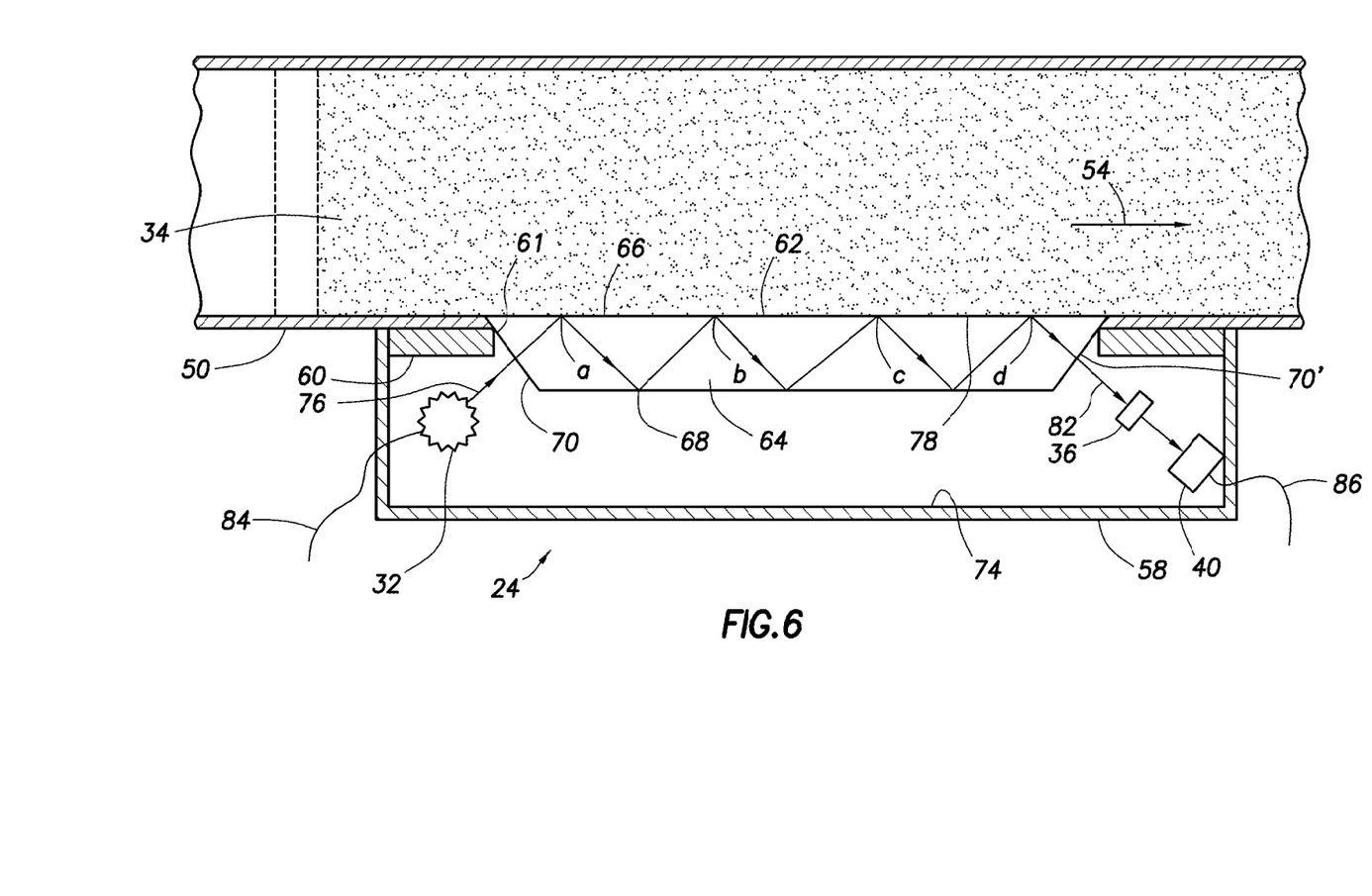
FIG. 6 is a sectional elevation view of a tube in which a sample is flowing and a representative of the MOE calculation device from FIG. 1, according to another embodiment.
Figure 7:
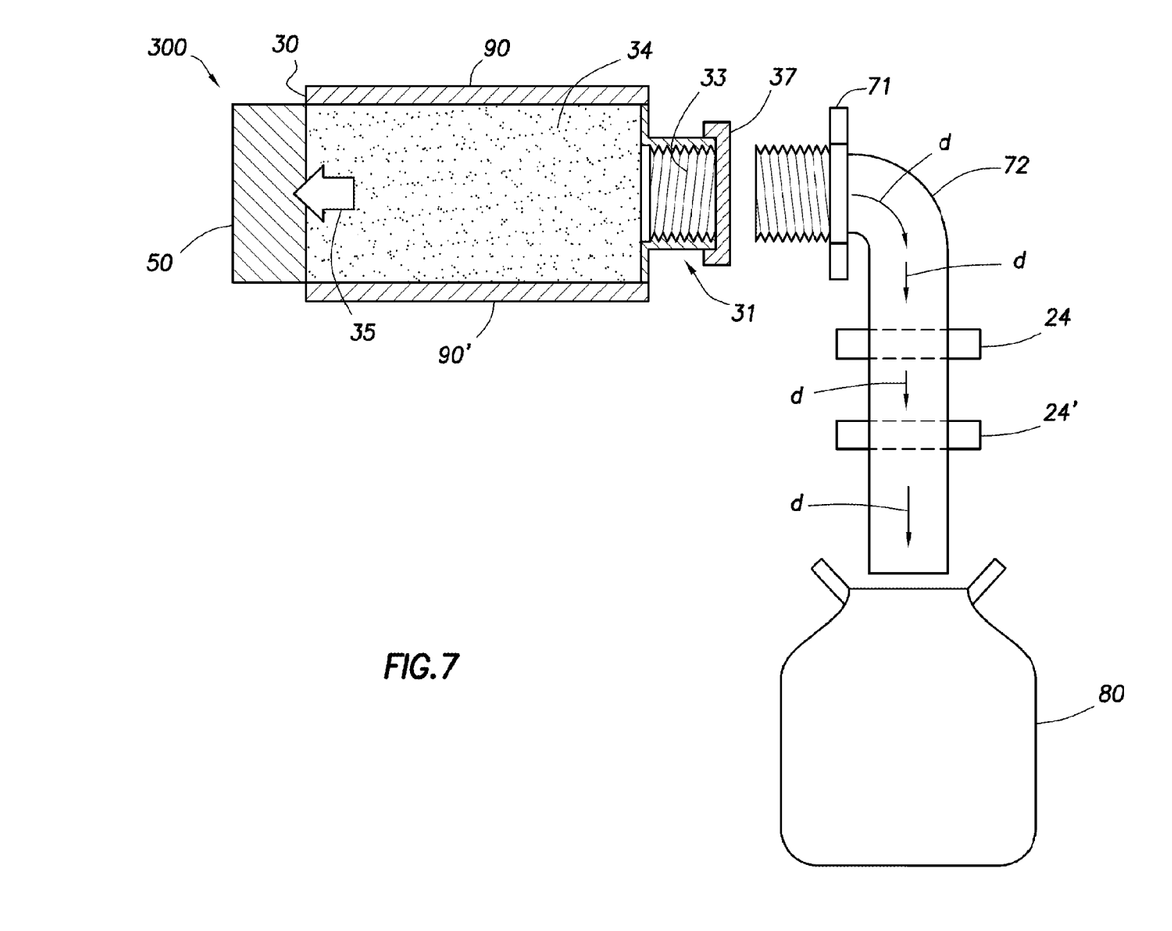
FIG. 7 illustrates an embodiment of placement of the MOE calculation device.

As can be seen in FIG. 2, the sample 34 may be located between the light source 32 and the MOE 36. According to another embodiment, and as depicted in FIG. 6, the sample 34 is located adjacent to the light source 32 and the MOE 36. In FIG. 6, a representative tube 50 may be part of an end of a sample receptacle 30 as depicted in FIG. 1, or it may be part of a transfer tube 72 as depicted in FIG. 7. The sample 34 can be flowing in the tube 50 in direction 54. Attached to the tube 50, which may be made of a variety of materials, including stainless steel, is an MOE calculation device 24. MOE calculation device 24 corresponds to the device 24 of FIG. 2 for determining the amount of a property of the sample 34 in the tube 50. The system utilizing the MOE calculation device 24 determines the amount of the property in real time and reports that amount instantaneously as it occurs in the sample 34 and simultaneously with other apparatuses (not shown) corresponding to MOE calculation device 24 attached to tube 50 adjacent to or at a given location in the tube and still other tubes corresponding to numerous samples in the field being monitored.

The MOE calculation device 24 comprises a housing 58, which may be magnetized metal or stainless steel, and a frame 60, which may be stainless steel, and which also may be magnetized and which may have appropriate protective coatings. The housing 58 and frame 60 may be circular, cylindrical, or rectangular. The housing is preferably constructed so that it is readily attachable and detachable from the tube 50. The tube 50 has a circular or rectangular opening 62 forming a window that is transparent to light including the IR spectrum. The housing 58 and frame 60 can be cylindrical, wherein the frame can form an internal circular opening 61.

An internal reflectance element (IRE) 64, which can be a circular optically transparent disc or rectangular optically transparent prism, or other shapes as may be used in a particular implementation, preferably of clear optically transparent diamond, or a pair of spaced optically transparent plates (not shown), is attached to the frame 60 in the frame opening 61 enclosing and sealing the opening 61. The IRE 64 may be bonded to the frame, for example, or attached in other ways as known in the art. The IRE 64 has two spaced parallel planar surfaces 66 and 68 and an outer annular inclined facet 70 defined by the Brewster angle, dependent upon the materials of the interface and wavelength of the light, to the surfaces 66 and 68. A Brewster angle (also known as the polarization angle) is an angle of incidence at which light with a particular polarization is perfectly transmitted through a transparent dielectric surface, with no reflection. A light source 32 is located in the housing cavity 74 and is located to cause its light 76 to be incident on the facet 70 at a right angle thereto. The facet is also at the Brewster angle or about 45° to the surface 78 of the sample 34 in the tube 50 contiguous with the IRE surface 66. The IRE 64 and frame 60 seal the pipe opening 61 in conjunction with a gasket such as an O-ring (not shown).

Located in the cavity 74 of the housing 58 is a MOE 36 and a detector 40 responsive to the output of the MOE 36 for generating an electrical intensity output signal whose value corresponds to a property of the sample to be determined. A conductor 84 supplies power to the light source 32 and a conductor 86 receives the detector output signal. Wires such as conductor 86 may be connected to a computer such as computer 12 of FIG. 2, located at a remote station for determining the property of the sample manifested by the signal on conductor 86. Alternatively, a battery, a local generator, or telemetry could also be used to power the apparatus components.

One problem with spectroscopy of raw petroleum or "oil" is the large absorbance of crude petroleum. Crude petroleum looks black because most of the light at all visible wavelengths is absorbed even by very small amounts of the petroleum. Some crude petroleums such as condensates and some "light" oils are more transparent in the visible wavelength range, but the majority of oils are dark. Experiments have shown that path lengths through which visible light must travel to obtain an optimum signal vary from 20 to 60 micrometers ($\mu$m). Experiments have shown that for dark oils, a 40 $\mu$m path length is acceptable. For the infrared region of absorption, optimum path lengths are a little longer as crude petroleum is more transparent in this region. However up to the electromagnetic region of 2.5 $\mu$m in the infrared, path lengths are still limited to between 100 and 300 $\mu$m (0.1 to 0.3 millimeters). Crude oil or petroleum, prior to treatment, is a dirty material containing both solid particles of varying diameters and multiphase "bubbles" (water in oil, oil in water, gas in oil, or gas in water). Both the solid particles and the "bubbles" have the capacity to clog a conventional absorption spectroscopy setup in which light is passed through a set of sampling windows to a detector.

One property of light as a wave is the ability of light to change its direction at a boundary through reflection. In reflection, the angle of reflection is equal to the angle of incidence as measured from the perpendicular of the boundary surface. At a given angle whether the wave will be transmitted or reflected in the optical domain is determined by the index of refraction of the materials at the boundary as well as the angle of incidence. For a system, reflection follows the behavior that the shallower the angle of incidence, the greater the chance of reflection and the greater the difference between index of refractions, the greater the chance for reflection. For some materials index of refraction may be chosen such that total internal reflectance is achieved and all light at almost any angle will be reflected. The exception is when light hits the boundary at the Brewster angle.

Using this principle, fiber optics carry light with little transmission loss through curved paths. Because the reflection occurs at the boundary which may have a very fine transition zone (angstrom level) which acts as sharp for light with a wavelength in the visible to infrared, the reflection actually takes place in the material behind the boundary from approximately 0.3 to 5 µm. This principle has led to the development of a spectroscopic sampling technique called total internal reflectance and makes use of a device called an internal reflectance element (IRE). In this device light is passed into a material of extremely high index of refraction usually diamond or sapphire. The light bounces between two boundaries, one containing the sample, and the other containing an optically transparent material. As light passes behind the sample boundary some of the light interacts with the sample as determined by normal spectroscopy. The total number of multiple reflections controlled by the element length is used to build any desired path length.

For instance at a one µm sampling depth, forty (40) reflections could build up a path length of forty (40) µm. Because the IRE sampling method does not suffer the constriction of a more conventional absorbance spectroscopy method, the device will not clog readily. IREs are commercially available.

In operation of the MOE calculation device 24 of FIG. 6, the light 76 from the source 32 is transmitted by the IRE 64 to the surface 78 of the sample 34 in the tube 50. It is known that the light 76 incident on and reflected from the sample surface will penetrate the surface a few micrometers, e.g., 0.3-5 µm, as discussed above. It is also known, as discussed above, that penetration of light into the sample must be to at least a depth of, or equivalent thereof, about 40 µm in order for the reflected interacted light from the sample surface 78 to carry sufficient wavelength information about the sample properties to be meaningful. Less penetration results in insufficient data being carried by the reflected interacted light to appropriately determine a property of the sample in the tube. The total path length requirements change depending upon the sample type, gas phase, water phase, the component being analyzed, and so on.

As a result, the light 76 from the source 32 is reflected from the sample surface 78 and which penetrates the surface to about 5 µm at location a. This reflected light from location a is interacted light and is reflected to the inner surface of surface 68 of the IRE 64 to produce further interacted light. Refraction indices of the diamond of the IRE 64 cause the interacted light to be reflected from the surface 68 back through the IRE to the sample surface 78 at location b, again penetrating to a depth of about 5 µm. This reflection process is repeated at locations c and d and other locations (not shown) until an accumulated depth of about 40 µm for all of the interactions is achieved. At the last location d, in this example, the reflected interacted light from the sample surface 78 is incident on IRE facet 70 at location 70'. Here the reflected light 82 is normal to the facet of the IRE 68 and passes through the facet 70'.

The light 82 is incident on the MOE 36 and passes through the MOE 36 to detector 40. It should be understood that a second detector (not shown) is also responsive to reflected light from the MOE and supplied to a further conductor (not shown) and thus to the computer such as computer 12 of FIG. 2, as described above.

It may be desirable to determine more than one property of the sample 34. The methods can further include the step of determining two or more properties of the sample 34. A separate MOE calculation device 24, as depicted as 24' in the Figures, is provided for each property to be determined. The IRE element 64 may have a thickness of about 1 to 2 mm and a diameter of about 10 to 20 mm when fabricated of diamond.

However, it should be understood that the distribution of light associated with the various light paths between the light source 32 and the IRE 64 is critical to the construction of the MOE 36. That is, different housings, sources attached to such housings, and IRE associated therewith all have unique light paths that may affect the light distribution. These light paths and distributions need to be taken into consideration during the MOE construction. This construction is based on a representative spectrum for the sample of interest. The intensities and distribution of the various wavelengths may vary from apparatus to apparatus, and thus, such light paths and distributions need to be taken into consideration in the design and construction of the MOE associated with a given apparatus.

This problem is resolved by using the housing 58, light source 32, and IRE 64 that is eventually to be utilized for the optics associated with a given MOE for use in generating the spectrum that is to be provided by a traditional spectrometer. That generated spectral data is then utilized to construct the MOE that is to be utilized with the associated housing, light, and IRE components. Thus, it is assured that the light paths and distributions from the installed housing, light source, and IRE are identical to those used to create the MOE; and thus, there will be no errors or problems in utilizing the MOE with such components. If such components ever need replacement, a new MOE needs to be constructed unique to those replacement components or otherwise compensated for changes in light distributions. Otherwise, an error in property determination may be possible if other components are utilized other than those used to create the MOE. Therefore, any components utilized in or that may affect the optical path lengths or wavelength distributions from light source to MOE need to be utilized to determine the spectral aspects of the property of interest used to construct the corresponding MOE.

The step of determining can be performed during or after the step of collecting. As can be seen in FIG. 1, the MOE calculation device 24 can be located at one end of the sample receptacle 30. The sample 34 can flow into the sample receptacle 30. In this manner, the MOE calculation device 24 can determine at least one property of the sample 34 as the sample is flowing into the sample receptacle 30. Of course, the MOE calculation device 24 can be designed such that it is capable of determining more than one property of the fluid. Moreover, there can be more than one sample container 300 and there can also be more than one MOE calculation device 24. If there is more than one sample container 300, then a first MOE calculation device 24 can be positioned adjacent to a first sample container 300 and a second MOE calculation device 24 can be positioned adjacent to a second sample container 300, etc. One MOE calculation device 24 can be designed to determine a first property of the sample, while another MOE calculation device 24 can be designed to determine a second property of the sample.

According to another embodiment, and as depicted in FIG. 7, the step of determining can be performed after the step of collecting. By way of example, it may be desirable to transfer a collected sample 34 into a different container. The methods can further include the step of transferring the sample 34 from the sample container 300 to a container 80, wherein the step of transferring can be performed after the step of collecting. This may be desirable, for example, if the sample container 300 does not meet transportation regulations and the sample needs to be transported off-site. As can be seen in FIG. 7, the sample 34 can be transferred to a container 80. The sample 34 can be transferred via a transfer tube 72. The transfer tube 72 can be connected to the sample container 300 in a variety of ways, for example, in a manner such that the sample 34 is capable of being removed from the sample receptacle 30 and placed into the container 80. By way of example, the sample container 300 can contain a male end 31 that is capable of connecting to a female end 71 of the transfer tube 72. The ends can be threaded together, for example, via threads 33 on the male end 31. The male end 31 can also include a seal 37. The seal 37 can be removed prior to attaching the transfer tube 72 to the sample container 300. The sample 34 can be transferred via a variety of means, for example, via a piston 50. This way, the sample 34 can flow from the sample receptacle 30, through the transfer tube 72, and into the container 80. The sample 34 can also be heated via one or more heating elements 90 and 90'.

The step of determining the at least one property of the sample 34 can be performed during the step of transferring the sample 34, for example during transference into the container 80. One or more MOE calculation devices 24 and 24' can be positioned adjacent to the transfer tube 72. In this manner, as the sample 34 is being transferred from the sample receptacle 30 into the container 80, the MOE calculation device 24 can determine the at least one property of the sample 34. As discussed above, a first MOE calculation device 24 can be designed to determine a first property of the sample 34 and a second MOE calculation device 24' can be designed to determine a second property of the sample. Moreover, one MOE calculation device 24 can be designed to determine two or more properties of the sample. There can also be more than two MOE calculation devices adjacent to the transfer tube 72.

The methods can further include the step of transporting one or more of the samples off-site, wherein the step of transporting can be performed after the step of determining. The results from the MOE calculation device 24 can be useful in deciding which, if any, of the samples might need to be transported off-site. By being able to determine at least one property of the sample, workers are able to more accurately determine which samples may require further analysis at an off-site location. The information obtained by using the MOE calculation device 24 on samples, particularly at a well site, can enable workers to obtain useful and oftentimes, essential information about the properties of a sample.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is, therefore, evident that the particular illustrative embodiments disclosed above may be altered or modified and all such variations are considered within the scope and spirit of the present invention. While compositions and methods are described in terms of "comprising," "containing," or "including" various components or steps, the compositions and methods also can "consist essentially of" or "consist of" the various components and steps. Whenever a numerical range with a lower limit and an upper limit is disclosed, any number and any included range falling within the range is specifically disclosed. In particular, every range of values (of the form, "from about a to about b," or, equivalently, "from approximately a to b,") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

What is claimed is:

1. A method of analyzing a fluid sample from an oil or gas reservoir comprising:
    collecting the sample in a sample container,
        wherein the step of collecting includes placing the sample container into a well,
        wherein the well penetrates a subterranean formation,
        wherein the oil or gas reservoir is the subterranean formation or is located adjacent to the subterranean formation,
        wherein the sample container includes a sample receptacle, and
        wherein the step of collecting comprises allowing or causing the sample to flow into the sample receptacle;
    removing the sample container from the well,
        wherein the step of removing is performed after the step of collecting;
    retrieving the sample receptacle from the sample container,
        wherein the step of retrieving is performed after the step of removing; and
    determining at least one property of the sample,
        wherein the step of determining comprises using a multivariate optical element (MOE) calculation device, and
        wherein the step of determining is performed during or after the step of collecting.

2. A method of analyzing a fluid sample from an oil or gas reservoir comprising:
    collecting the sample in a sample container,
        wherein the step of collecting includes placing the sample container into a well,
        wherein the well penetrates a subterranean formation,
        wherein the oil or gas reservoir is the subterranean formation or is located adjacent to the subterranean formation,
        wherein the sample container includes a sample receptacle,
        wherein the step of collecting comprises allowing or causing the sample to flow into the sample receptacle, and
        wherein the sample is contained inside the sample receptacle until such time when it is desirable to remove the sample from the sample receptacle;
    removing the sample container from the well,
        wherein the step of removing is performed after the step of collecting; and
    determining at least one property of the sample,
        wherein the step of determining comprises using a multivariate optical element (MOE) calculation device, and
        wherein the step of determining is performed during or after the step of collecting.

3. A method of analyzing a fluid sample from an oil or gas reservoir comprising:
   collecting the sample in a sample container,
      wherein the step of collecting includes placing the sample container into a well,
      wherein the well penetrates a subterranean formation,
      wherein the oil or gas reservoir is the subterranean formation or is located adjacent to the subterranean formation,
      wherein the sample container includes a sample receptacle, and
      wherein the step of collecting comprises allowing or causing the sample to flow into the sample receptacle;
   removing the sample container from the well;
      wherein the step of removing is performed after the step of collecting; and
   determining at least one property of the sample,
      wherein the step of determining comprises using a multivariate optical element (MOE) calculation device, and
      wherein the step of determining is performed during the step of collecting, and
      wherein the MOE calculation device is located at one end of the sample receptacle.

4. The method according to claim 3, wherein the sample is a reservoir fluid.

5. The method according to claim 3, wherein the at least one property of the sample is selected from the group consisting of: asphaltenes; saturates; resins; aromatics; solid particulate content; hydrocarbon composition and content; gas composition $C_1$-$C_{13}$ and content; carbon dioxide; hydrogen sulfide gas; and correlated pressure, volume, temperature properties including gas-to-oil ratio, bubble point, density, a petroleum formation factor, viscosity, a gas component of a gas phase of a petroleum, total stream percentage of water, gas, oil, solid particles, solid types, oil finger printing, reservoir continuity, oil type; and water elements including ion composition and content, anions, cations, salinity, organics, pH, mixing ratios, tracer components, contamination; or other hydrocarbon, gas, solids, or water properties that can be related to spectral characteristics using regression methods.

6. The method according to claim 3, wherein the MOE calculation device comprises: a light source; a multivariate optical element (MOE); a reflected light detector, wherein the reflected light detector detects light reflected from MOE; and a transmitted light detector, wherein the transmitted light detector detects light transmitted by MOE.

7. The method according to claim 6, wherein the sample is located between the light source and the MOE.

8. The method according to claim 6, wherein the sample is located adjacent to the light source and the MOE.

9. A method of analyzing a fluid sample from an oil or gas reservoir comprising:
   collecting the sample from a well in a sample container,
      wherein the well penetrates a subterranean formation, and
      wherein the oil or gas reservoir is the subterranean formation or is located adjacent to the subterranean formation; and
   determining two or more properties of the sample,
      (A) wherein the step of determining comprises using a multivariate optical element (MOE) calculation device,
      wherein the step of determining is performed during or after the step of collecting,
      (B) wherein the two or more properties of the sample are selected from the group consisting of: asphaltenes; saturates; resins; aromatics; solid particulate content; hydrocarbon composition and content; gas composition $C_1$-$C_{13}$ and content; carbon dioxide; hydrogen sulfide gas; and correlated pressure, volume, temperature properties including gas-to-oil ratio, bubble point, density, a petroleum formation factor, viscosity, a gas component of a gas phase of a petroleum, total stream percentage of water, gas, oil, solid particles, solid types, oil finger printing, reservoir continuity, oil type; and water elements including ion composition and content, anions, cations, salinity, organics, pH, mixing ratios, tracer components, contamination; or other hydrocarbon, gas, solids, or water properties that can be related to spectral characteristics using regression methods, and
      (C) wherein the MOE calculation device is designed such that it is capable of determining the two or more properties of the sample.

10. A method of analyzing a fluid sample from an oil or gas reservoir comprising:
   collecting the sample from a well in a sample container,
      wherein the well penetrates a subterranean formation, and
      wherein the oil or gas reservoir is the subterranean formation or is located adjacent to the subterranean formation;
   transferring the sample from the sample container to a container,
      wherein the step of transferring is performed after the step of collecting; and
   determining at least one property of the sample,
      wherein the step of determining comprises using a multivariate optical element (MOE) calculation device, and
      wherein the step of determining is performed during or after the step of collecting.

11. The method according to claim 10, wherein the step of determining the at least one property of the sample is performed during the step of transferring the sample.

12. The method according to claim 11, wherein the sample is transferred to the container via a transfer tube.

13. The method according to claim 12, wherein one or more MOE calculation devices are positioned adjacent to the transfer tube.

14. The method according to claim 10, wherein the sample is a reservoir fluid.

15. The method according to claim 10, wherein the MOE calculation device comprises: a light source; a multivariate optical element (MOE); a reflected light detector, wherein the reflected light detector detects light reflected from MOE; and a transmitted light detector, wherein the transmitted light detector detects light transmitted by MOE.

16. The method according to claim 15, wherein the sample is located between the light source and the MOE.

17. The method according to claim 15, wherein the sample is located adjacent to the light source and the MOE.

* * * * *